United States Patent [19]

Lovett

[11] Patent Number: 5,162,206

[45] Date of Patent: Nov. 10, 1992

[54] PLASMIDS FOR FOREIGN GENE EXPRESSION IN B. SUBTILIS

[75] Inventor: Paul S. Lovett, Columbia, Md.

[73] Assignee: University of Maryland, Baltimore, Md.

[21] Appl. No.: 683,490

[22] Filed: Apr. 9, 1991

Related U.S. Application Data

[63] Continuation of Ser. No. 317,070, Feb. 24, 1989, abandoned, which is a continuation of Ser. No. 686,625, Dec. 31, 1984, abandoned, which is a continuation of Ser. No. 479,167, Mar. 28, 1983, abandoned, which is a continuation of Ser. No. 307,604, Oct. 1, 1981, abandoned.

[51] Int. Cl.$^5$ ............ C12P 21/00; C12N 15/63; C12N 15/74; C12N 15/75; C07H 15/10
[52] U.S. Cl. .................. 435/69.1; 435/172.3; 435/320.1; 435/252.31; 435/252.3; 536/27; 935/74; 935/29; 935/23; 935/38
[58] Field of Search ............ 435/172.3, 317.1, 252.31, 435/252.3, 320.1, 69.1, 69.7

[56] References Cited

U.S. PATENT DOCUMENTS 4,237,224 12/1980 Cohen et al. .................... 435/69.1

FOREIGN PATENT DOCUMENTS 2048894 12/1980 United Kingdom ................ 435/172

OTHER PUBLICATIONS

Freifelder, D. 1983, in: *Molecular Biology*—a Comprehensive Introduction to Prokaryotes and Eukaryotes, Van Nostrand Reinhold Co., p. 703.
Gryczan et al., J. Bact. vol. 141, pp. 246-253, Jan. 1980.
Gryczan et al., PNAS, USA, vol. 75, pp. 1428-1432, Mar. 1978.
Ehrlich, PNAS, USA, vol. 75, pp. 1433-1436, Mar. 1978.
Keggins et al., PNAS, USA, vol. 75, pp. 1423-1427, Mar. 1978.
Gray et al., J. Bact., vol. 145, pp. 422-428 (Jan. 1981).
Williams et al., J. Bact., vol. 146, pp. 1162-1165, Jun. 1981.
Wu, Methods in Enzymology, vol. 68, pp. 342-357 (1979).
Gray et al., Mol. Gen. Genet., vol. 177, pp. 459-467 (1980).
Duncan et al., Chem. Abst., vol. 86:185728k, 1977.
Chakrabarty, Genetic Engineering CRC Press, pp. 145-157 (1978).
Boyer et al., Genetic Engineering, Elsevier/North Holland Biomedical Press, pp. 25-45 (1978).
Marrero et al., J. Bacteriology, vol. 143, pp. 879-886 Aug. 1980.
Goebel et al., Nucleic Acids, Proteins, Proc. Sym., pp. 529-539, Scientific Press, Peking, Peoples Republic of China, entitled "Molecular Cloning in *Bacillus Subtilis*" (1979).

*Primary Examiner*—Robert A. Wax
*Assistant Examiner*—Christopher S. F. Low
*Attorney, Agent, or Firm*—Scully, Scott, Murphy & Presser

[57] ABSTRACT

A double-stranded DNA plasmid which includes a promoter DNA sequence that is not derived from a *B. subtilis* plasmid and a DNA sequence derived from a *B. subtilis* plasmid is useful for introducing into *B. subtilis* foreign DNA having a nucleic acid sequence which does for the production of a desired product. Preferably, the promoter sequence is also not derived from *B. subtilis* chromosomal DNA. When a foreign DNA sequence having a nucleic acid sequence coding for production of a desired product is introduced into this plasmid, another plasmid is produced which is useful for effecting expression in *B. subtilis* of the foreign DNA and production of the desired product. The plasmids may additionally include an inducible gene.

*B. subtilis* cells transformed with plasmids carrying a gene or genes coding for the production of desired products may be grown in culture and the resulting products recovered.

17 Claims, 3 Drawing Sheets

PLASMIDS FOR FOREIGN GENE EXPRESSION IN B. SUBTILIS

The present application is a continuation of U.S. Ser. No. 317,070 filed Feb. 24, 1989, now abandoned; which is a continuation of U.S. Ser. No. 686,625, filed Dec. 31, 1984, now abandoned; which is a continuation of U.S. Ser. No. 479,167 filed Mar. 28, 1983, now abandoned; which is a continuation of U.S. Ser. No. 307,604 filed Oct. 1, 1981, now abandoned.

BACKGROUND OF THE INVENTION

Considerable interest exists in the application of genetic engineering techniques for the production of commercially valuable products such as insulin, human and animal growth hormones and enzymes. Much of the work to date has involved use of *Escherichia coli* as the host into which foreign genetic material is introduced. Expression of the genetic material in *E. coli* results in production of desired products. When combined with growth of genetically engineered cells in culture, it permits production of the desired products in commercially meaningful yields. Unfortunately, use of *E. coli* as a host is associated with certain disadvantages. As a result, alternative hosts, including other bacteria and yeast, are under investigation.

One particularly promising host for commercial applications of genetic engineering is *Bacillus subtilis*. *B. subtilis* is a non-pathogenic, gram positive bacterium which is eaten daily by millions of Japanese as part of a fermented soybean product. *B. subtilis* may be the safest bacterium in which to achieve expression of foreign genes whose products, e.g. interferon, will be purified and subsequently injected into humans for at least two reasons. First, *B. subtilis* is known to be non-pathogenic. Secondly, *E. coli* is known to produce endotoxins which may contaminate genetic products and induce endotoxic shock in humans.

Direct expression in *Bacillus subtilis* of a gene originating in *Escherichia coli* has been achieved in a single reported case [Rubin, E. M., et al., Gene 10:227–235 (1980)] There the *E. coli* gene specifying thymidylate synthetase expressed upon integration into the *B. subtilis* chromosome. However, *E. coli* genes residing on plasmids typically do not express at the level of genetic function in *B. subtilis*. [Kreft, J., et al., Mol. Gen. Genet. 162:59–67 (1978)]. The least complex explanation for the lack of foreign gene expression in *B. subtilis* is an absence of correct transcription and/or translation. In vitro transcription studies have indicated that *E. coli* RNA polymerase is significantly more efficient in initiating transcription from an *E. coli* promoter than is the *B. subtilis* RNA polymerase [Lee, G., et al., Mol Gen. Genet. 180:57–65 (1980)]. It was therefore suspected that inserting an *E. coli* gene, or other foreign gene, into a segment of DNA known to be efficiently transcribed in *B. subtilis* might permit functional expression of the foreign DNA.

SUMMARY OF THE INVENTION

A double-stranded DNA plasmid which includes a promoter DNA sequence not derived from *B. subtilis* plasmid DNA and a DNA sequence derived from a *B. subtilis* plasmid is useful for introducing into *B. subtilis* foreign DNA which includes a gene coding for the production of a desired product. Preferably, the promoter DNA sequence is not derived from *B. subtilis*. Examples of suitable sources of the promoter include bacteriophages SP02 and Φ105, *B. pumilus* plasmid pPL10 and *B. licheniformis*. The plasmid may be linear or circular and may additionally include an inducible gene such as a chloramphenicol inducible gene coding for synthesis of chloramphenicol acetyltransferase.

A double-stranded DNA plasmid which includes a promoter DNA sequence which is not derived from *B. subtilis*, a DNA sequence derived from a *B. subtilis* plasmid and foreign DNA which includes a gene coding for the production of a desired product such as a polypeptide and which is capable of expression when the plasmid is introduced into *B. subtilis* is useful in the production of the desired products for which the foreign DNA codes.

*B. subtilis* cells which contain the plasmids are novel. They may be grown in culture to produce commercially valuable materials which can then be recovered.

DETAILED DESCRIPTION OF THE INVENTION

Figure 1:
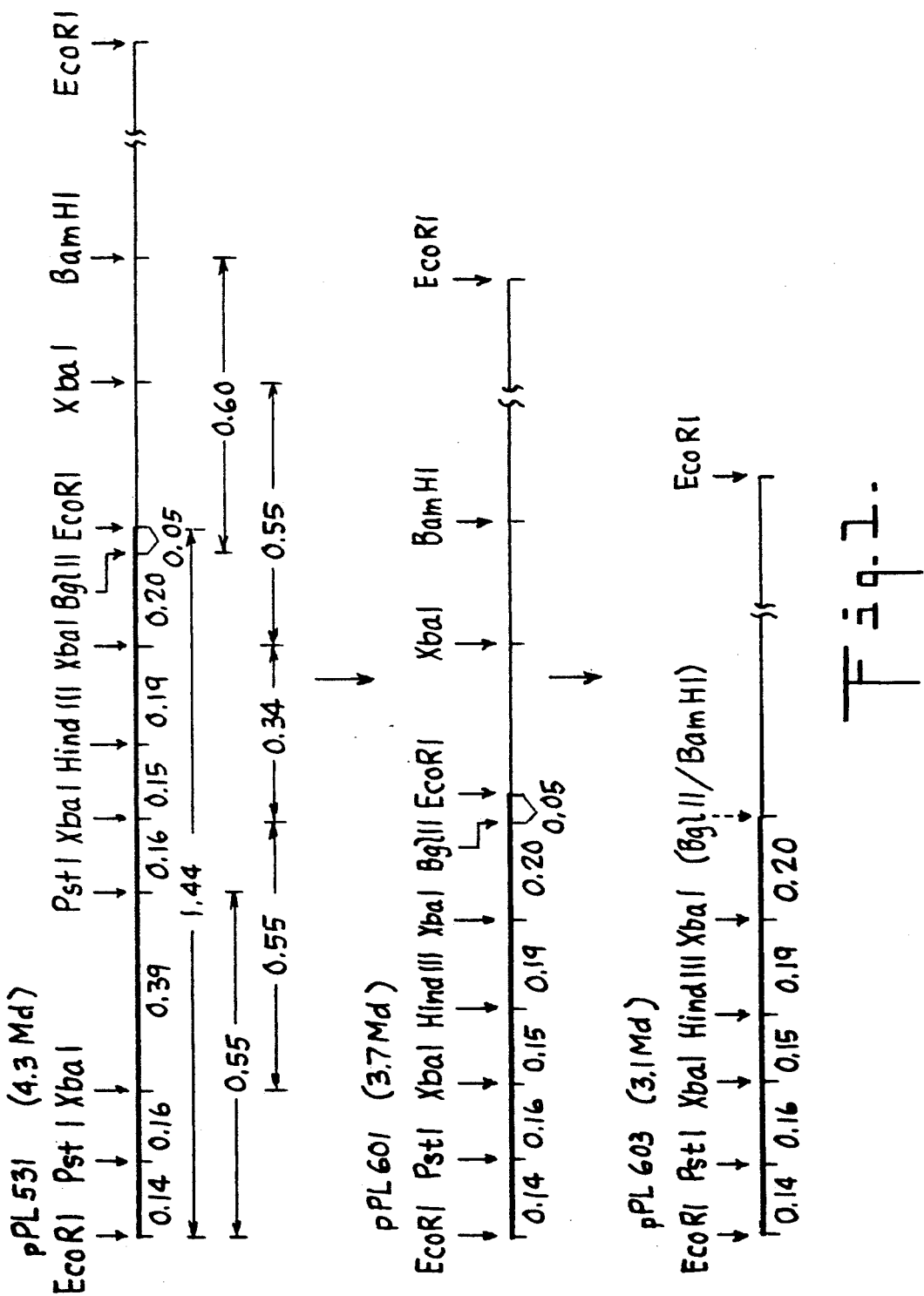
FIG. 1 shows the restriction endonuclease maps of three plasmids, pPL531, pPL601 and pPL603. The thickened horizontal line indicates the cloned *B. pumilus* DNA in each plasmid.

Plasmids have been created which are useful for the introduction into *Bacillus subtilis* of foreign DNA whose nucleic acid sequence includes one or more genes encoding the information necessary for production of desired products, particularly polypeptide or partially polypeptide products such as insulin, α-thymosin, growth hormones, enzymes, antibodies and the various interferons. These plasmids are double-stranded DNA molecules which include a promoter DNA sequence which is not derived from *B. subtilis* plasmid DNA and a DNA sequence which is derived from a *B. subtilis* plasmid. These plasmids may be linear or circular. However, when used for bacterial transformation, they will generally be circular.

The promoter DNA sequence is preferably not derived from *B. subtilis* chromosomal DNA, but rather from another source. Numerous suitable sources are available, including the bacteriophages SP02 and Φ105, the *B. pumilus* plasmid pPL10 and *B. licheniformis*. The origin of the DNA from a *B. subtilis* plasmid may likewise vary widely, any *B. subtilis* strain being capable of functioning as a source of the plasmid DNA. One example of a suitable source is the *B. subtilis* plasmid pUB110.

These plasmids may additionally include an inducible gene such as a drug inducible gene to facilitate selection of cells carrying the plasmid and increased gene expression in the cells so selected. Illustrative of such inducible genes are a chloramphenicol-inducible gene coding for synthesis of chloramphenicol acetyltransferase. One such gene may be obtained from B. pumilus NCIB 8600.

Additional plasmids have been constructed which are useful for effecting expression in Bacillus subtilis of DNA which does not naturally occur in B. subtilis and which has a nucleic acid sequence which includes one or more genes associated with the production of desired products or the expression of useful properties. These plasmids are double-stranded, deoxyribonucleic acid molecules which include a promoter DNA sequence which is not derived from B. subtilis plasmid DNA, a DNA sequence derived from a B. subtilis plasmid and foreign DNA having a sequence coding for the production of a desired product. These plasmids may be linear or circular, although they are generally circular when used in bacterial transformation.

The promoter DNA sequence is preferably not derived from B. subtilis chromosomal deoxyribonucleic acid, but from a source other than B. subtilis. Although numerous sources are available, suitable sources include bacteriophages SP02 and Φ105, the B. pumilus plasmid pPL10 and B. licheniformis. Of these, a promoter obtained from SP02 is presently preferred.

The DNA derived from a B. subtilis plasmid may be obtained from any such plasmid. At present, the preferred source is the B. subtilis plasmid pUB110.

Foreign DNA which includes a gene or genes associated with production of a desired product may be obtained from any appropriate source or may be chemically synthesized. Examples of suitable foreign DNA sequences include mammalian genes coding for interferon and genes coding for insulin, enzymes, growth hormones, viral antigens and the like.

The plasmids may also include an inducible gene such as a chloramphenicol-inducible gene coding for the synthesis of chloramphenicol acetyltransferase.

Methods for identifying, recovering and purifying the various DNA segments which are portions of the plasmids are known to those skilled in the art as are methods for ligating the segments, transforming bacterial cells, cloning and recovering products synthesized. Accordingly, the methods will only be described by reference to specific embodiments of the invention set forth hereinafter.

Certain of the experimental details which follow were reported in Williams, D. M., Duvall, E. J. and Lovett, P. S., J. Bacteriology, 146:1162–1165, June 1981. To show the state of the art, the disclosure thereof is hereby incorporated by reference into this specification.

DNA preceding structural genes contains regulatory sites essential to gene expression, including sequences necessary for initiation of transcription and translation. Selective expression of genes involved in the developmental process of bacterial sporulation may be partially controlled by the occurrence of sporulation-specific regulatory sequences that participate in modulating sporulation gene expression. A direct approach to isolate regulatory sequences from DNA was provided by the developmennt of plasmid vectors [Clowes, R. C. Bacteriol. Rev. 36:361–405 (1972)] useful for cloning DNA segments that act as promoters and translation initiation signals in Escherichia coli [An, G., and Friesen, J. D., J. Bacteriol. 140:400–410 (1979); Casadaban, M. J., et al., J. Bacteriol. 143:971–980 (1980); and Casadaban, M. and Cohen, S. N., J. Mol. Biol 138:179–207 (1980)]. The potential value of similar cloning vectors for the Bacillus subtilis system prompted screening for a structural gene that was potentially capable of expression in B. subtilis, but appeared to lack those regulatory controls needed for expression. A description follows of the development of a plasmid cloning vector that permits direct selection for cloned fragments of DNA which are necessary to the expression of a chloramphenicol acetyltransferase gene in B. subtilis.

Plasmid pPL531 was generated by cloning into the 3-megadalton, neomycin-resistance plasmid pUB110 [Gryczan, T. J., et al., J. Bacteriol. 134:318–323 (1978); Sadaie, Y., et al., J. Bacteriol. 141:1178–1182 (1980)] a 1.44-Md, EcoRI-generated fragment from DNA isolated from a chloramphenicol-resistant (Chr$^r$) derivative of Bacillus pumilus NCIB 8600, using methods previously described. [Lovett, P. S. and Keggins, K. M., Methods Enzymol. 68:342–357 (1979)]. pPL531 (shown in FIG. 1) confers on host cells, e.g., BR151, resistance to both neomycin (10 μg/ml) and Chr.

Plasmid pPL600 is a derivative of pPL531 in which the orientation of the Chr$^r$ fragment was reversed by EcoRI cleavage and ligation. BR151 harboring either pPL531 or pPL600 grew in Penassay broth (PB; Difco Laboratories) containing up to 200 μg of Chr per ml (higher levels were not tested). Cells harboring both plasmids produced chloramphenicol acetyltransferase (Table I). BR151(pPL531) or BR151(pPL600) grown on 5 μg of Chr per ml produced approximately 10-fold higher levels of chloramphenicol acetyltransferase than cells grown in the absence of the drug (Table I). Deletion of the PstI fragment (~0.55 Md) from pPL531 generated plasmid pPL601 (FIG. 1; Table I). BR151(pPL601) was incapable of growth in PB containing 25 μg of Chr per ml, although normal growth was observed in 5 μg of Chr per ml, and sparse growth was observed in 10 μg of the drug per ml. The specific activity of chloramphenicol acetyltransferase in BR151(pPL601) grown in PB containing 5 μg of Chr per ml was 20-fold lower than the activity produced by BR151 (pPL531) (Table I). Reversal of the orientation of the insert in pPL601 or deletion of the PstI fragment from pPL600 generated pPL602 which, in BR151, conferred resistance to 200 μg of Chr per ml (Table I).

TABLE I

CHLORAMPHENICOL RESISTANCE PROPERTIES OF pPL531 AND DERIVATIVE PLASMIDS

| Plasmid | Insert mol wt (10$^6$) | Source of insert | Chloramphenicol acetyltransferase sp act$^a$ −Chr | Chloramphenicol acetyltransferase sp act$^a$ +Chr | Maximum Chr$^b$ (μg/ml) |
|---|---|---|---|---|---|
| pPL531 | | | 0.04 | 0.52 | 200 |
| pPL600 | | | 0.09 | 0.96 | 200 |
| pPL601 | | | 0.01 | 0.03 | 5 |
| pPL602 | | | 0.04 | 0.71 | 200 |
| pPL603 | | | 0.01 | 0.04 | 5 |
| pPL604 | 1.3 | EcoRI* of pUB110 | 0.33 | 4.37 | 200 |
| pPL605 | 0.54 | EcoRI* of pPL10 | 0.03 | 0.29 | 100 |
| pPL608 | 0.21 | EcoRI* of SP02 | 0.21 | 4.02 | 200 |
| pPL613 | 0.15 | EcoRI of B. licheniformis | 0.63 | 2.1 | 200 |
| pPL614 | 1.0 | EcoRI of | 0.34 | 0.68 | 100 |

TABLE I-continued

CHLORAMPHENICOL RESISTANCE PROPERTIES
OF pPL531 AND DERIVATIVE PLASMIDS

| Plasmid | Insert mol wt (10[6]) | Source of insert | Chloramphenicol acetyltransferase sp act[a] −Chr | +Chr | Maximum Chr[b] (μg/ml) |
|---|---|---|---|---|---|
| | | B. licheniformis | | | |

[a]Chlroamphenicol acetyltransferase activity [Shaw, W. V., Methods Enzymol. 43:737-755 (1978)] was assayed in extracts from cells grown in PB containing no Chr (−Chr) or 5 μg of Chr (+Chr) per ml. Protein was measured by the method of Bradford [Bradford, M. M., Anal. Biochem. 72:248-254 (1976)].

[b]Approximately 10[7] plasmid-containing cells previously grown in PB containing 5 μg of Chr per ml were inoculated into 2 ml of PB containing Chr at 5, 10, 25, 50, 100 or 200 μg/ml. Incubation proceeded for 20 hours, at which time the maximum concentration of Chr allowing growth was recorded.

Since pPL602 did confer high-level Chr[r], it was evident that an intact structural gene for chloramphenicol acetyltransferase was present on the cloned EcoRI fragment after the internal PstI deletion was made. Moreover, the inability of pPL601 to confer high-level Chr[r] suggested that expression in pPL602 was dependent on some property of the vector plasmid pUB110. For example, if the PstI deletion removed a promoter region from the cloned fragment, expression of the gene would be dependent on a pUB110 promoter. Hence, chloramphenicol acetyltransferase activity would only be expressed when the structural gene was correctly oriented relative to the external promoter. In pPL602, the gene is expressed, and therefore the orientation would be correct. In pPL601, the orientation is incorrect, and the gene is unexpressed or very weakly expressed.

Cloning BamHI or MboI fragments of *Bacillus licheniformis* DNA into the BamHI site on pPL601 failed to permit pPL601 to transform BR151 to Chr[r] (selection on tryptose blood agar base containing 10 μg of Chr per ml). Cloning PstI fragments of the same DNA into pPL601 allowed pPL601 to successfully generate numerous Chr[r] transformants of BR151, suggesting that inserts left of the PstI site of pPL601 (shown in FIG. 1) might promote chloramphenicol acetyltransferase activity. Accordingly, the BamHI proximal EcoRI site on pPL601 was deleted by BamHI and BglII digestion, ligation, and transformation of BR151 with selection for Neo[r]. A resulting plasmid which retained a single EcoRI site was designated pPL603 (FIG. 1; Table I). EcoRI* or EcoRI activity [Polisky, B. P., et al., Proc. Natl. Acad. Sci., U.S.A. 72:3310-3314 (1975)] was used to digest pPL10, pUB110, and DNA from *B. licheniformis* 9945A and phage SP02 (Hemphill, H. E. and Whiteley, H. R., Bacteriol. Rev. 39:257-315 (1975); Lovett, P. S., et al., J. Bacteriol. 127:817-828 (1976); Scher, B. M., et al, J. Virol. 28:395-402 (1978); and Yoneda, Y., et al., Gene 7:51-68 (1979)]. Approximately 1 μg of EcoRI*- or EcoRI-digested DNA was mixed with 1 μg of EcoRI-digested pPL603 in 100 μl. The ligated DNA (approximately 2 μg) was shaken with 3×10[8] competent [Bott, K. F. and Wilson, G. A., J. Bacteriol. 94:562-570 (1967)] *B. subtilis* cells for 1 hour and plated directly onto tryptose blood agar base containing 10 μg of Chr per ml. About 200 to 600 Chr[r] transformants were obtained per μg of input DNA. Each of more than 200 Chr[r] transformants was neomycin resistant, and each of a total of 83 examined by the single colony lysis-gel electrophoresis procedure contained plasmid having a molecular weight greater than pPL603. A derivative of pPL603 containing an EcoRI* or an EcoRI fragment cloned from each of the above DNA species was further examined. pPL604 is the designation for a pPL603 derivative containing a 1.3-megadalton EcoRI* fragment of pUB110 DNA. pPL604 was cloned and maintained in BR151R, a recE4 derivative of BR151, because of the homology between the cloned fragment and a portion of pPL603. pPL604 conferred on BR151R the ability to grow in 200 μg of Chr per ml, and the cells produced a high level of chloramphenicol acetyltransferase (Table I). Removal of the insert regenerated a plasmid indistinguishable from pPL603 in size and Chr sensitivity. One of these derivatives of pPL604 from which the insert had been removed was subsequently used to clone EcoRI fragments of Φ105 DNA to determine whether the exicision process had altered the ability of the chloramphenicol acetyltransferase gene to produce high-level resistance. There appeared to be no difference between this plasmid and pPL603 in terms of the ability of inserts to promote Chr[r]. Relevant data for fragments cloned in pPL603 from EcoRI* digests of pPL10 and SP02 and EcoRI digests of *B. licheniformis* DNA are shown in Table I. In each case, removal of the cloned insert regenerated a plasmid comparable to pPL603.

EcoRI fragments of *B. subtilis* DNA were cloned into pPL603 by as procedure differing from the above only in that the transformation recipient was a recE4 derivative of BR151, BR151R, and the protoplast transformation system was used [Chang, S. and Cohen, S. N. Mol. Gen. Genet. 160:111-115 (1979)]. By this procedure, the frequency of Chr[r] trahsformants was on the order of 1,000 per μg of input DNA. Each of more than 40 transformants examined contained pPL603 harboring an insert.

Three classes of DNA fragments were identified on the basis of ability to promote expression of Chr[r] when inserted into pPL603. The EcoRI-generated trpC complementing fragment previously cloned from *B. pumilus* [Keggins, K. M., et al., J. Bacteriol. 134:514-520 (1978); and Keggins, K. M., et al., Proc. Natl. Acad. Sci, U.S.A. 75:1423-1427 (1978)] did not promote Chr[r] when inserted into pPL603 in either orientation, although trpC complementing activity was expressed in both orientations. EcoRI fragment F of Φ105 DNA [Cully, D. F. and Garro, A. J., J. Virol. 34:789-791 (1980)] promoted Chr[r] in one orientation (pPL615) but not in the reverse orientation (pPL616). However, the Φ105 immunity property of fragment F was expressed in both orientations. Lastly, the EcoRI* fragment cloned from pPL10 into pPL603 [chimera, designated pPL605 (shown in Table I)] promoted Chr[r] in either orientation. Orientations of all inserts were judged by Hind III cleavage patterns.

Sequences that promote Chr[r] expression have been cloned from a variety of DNA sources, and it therefore is likely that these contain regulatory signals common to many genes. Whether these regulatory signals exert their control at the transcriptional or translational level remains to be determined.

The recombinant vector plasmid, pPL603, contains an unexpressed CAT gene preceded by a unique EcoRI site and permits the direct cloning of DNA fragments that have promoter activity in *B. subtilis*. Promoter fragments cloned into the unique EcoRI site result in high level expression of the CAT gene. The cloned promoter in plasmid pPL608 described. more fully hereinafter is capable of permitting expression of both foreign procaryotic and eucaryotic genes in *B. subtilis*.

pPL608 is therefore the first vector plasmid for *B. subtilis* capable of expressing cloned procaryotic and eucaryotic genes.

CLONING *E. COLI* TRP GENES IN *B. SUBTILIS*

In order to determine whether splicing a gene not normally expressed in *B. subtilis* into the cloned CAT gene in pPL608 would allow expression of the foreign DNA, the Hind III site was chosen for cloning because inserts at this location were found to inactivate all CAT activity.

Figure 2:
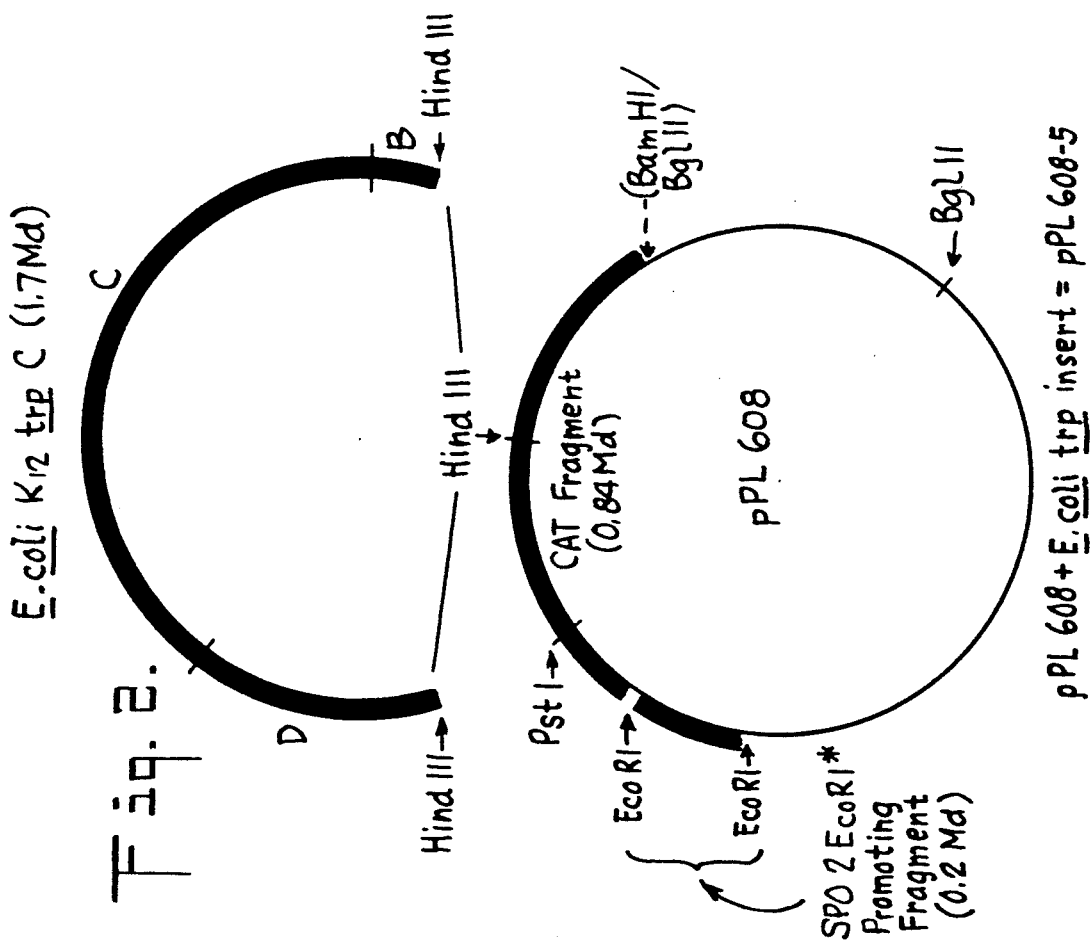
FIG. 2 is a diagram of the insertion and orientation of the 1.7 Md *E. coli* trpC fragment in pPL608-5. Orientation of the fragment was determined from double digests of pPL608-5 with Hinc II and EcoRI.

The Hind III generated DNA fragment spanning the *E. coli* trpC gene was cloned into pPL608 from HB101 chromosome DNA and pVH5 (See Materials and Methods which follow for details). Composite plasmids containing a trp insert cloned from chromosome digest (pPL608-3) or a digest of pVH5 (pPL608-5) were distinguishable by several criteria. Therefore, relevant properties for only pPL608-5 are described. pPL608-5 (5.0 Md, shown in FIG. 2) complemented mutations in trpD, trpC and trpF genes of *B. subtilis*, but not mutations in trpE, trpB, or trpA. Removal of the 1.7 Md insert from pPL608-5 by Hind III cleavage and ligation, regenerated the Chr$^r$ phenotype of the vector and deleted the trp D C F complementing activity. The 1.7 Md cloned insert in pPL608-5 and pPL608-3 comigrated with a Hind III fragment of pVH5. Nick translated pVH5 hybridized to the 1.7 Md fragment in Hind III digests of pPL608-5 and 608-3, demonstrating identity among the 1.7 Md fragments in the plasmids. In this experiment, approximately 1 µg of digested plasmid was subjected to electrophoresis as described previously, [Marrero, R. and Lovett, P. S., J. Bacteriol. 143:879–886 (1980)]. Hind III digested DNA was employed as reference. The gel was blotted to nitrocellulose paper to which was hybridized nick translated pVH5.

In order to test whether sequences in pPL608 were essential to the expression of the cloned *E. coli* trp fragment, the orientation of the trp fragment was reversed by Hind III cleavage and ligation. Each of three plasmids which were Chr$^s$ and did not complement trpC2 in BD224 contained the 1.7 Md trp insert in the reverse orientation as judged by digestions with Hinc II and EcoRI endonucleases. Secondly, removal of the 0.2 Md promoting fragment from pPL608-5 by EcoRI cleavage and ligation resulted in loss of trpC complementing activity in BD224. Lastly, the 1.7 Md trp fragment was transferred from pPL608-5 to the single Hind III site in a joint vector constructed by ligating pBR322 and pUB110 at their EcoRI sites. This plasmid complemented the trpC mutation in *E. coli* strain IC888, but did not complement the trpC2 mutation in BD224 within 36 hour incubation at 37° C. However, prolonged incubation (72 hours) of BD224 harboring such composite plasmids did result in sparse growth on tryptophan-free media. Accordingly, sequences present in pPL608 appear essential to expression of the cloned *E. coli* trpC gene.

CHLORAMPHENICOL INDUCTION OF *E. COLI* trpC EXPRESSION IN pPL608-5

Figure 3:
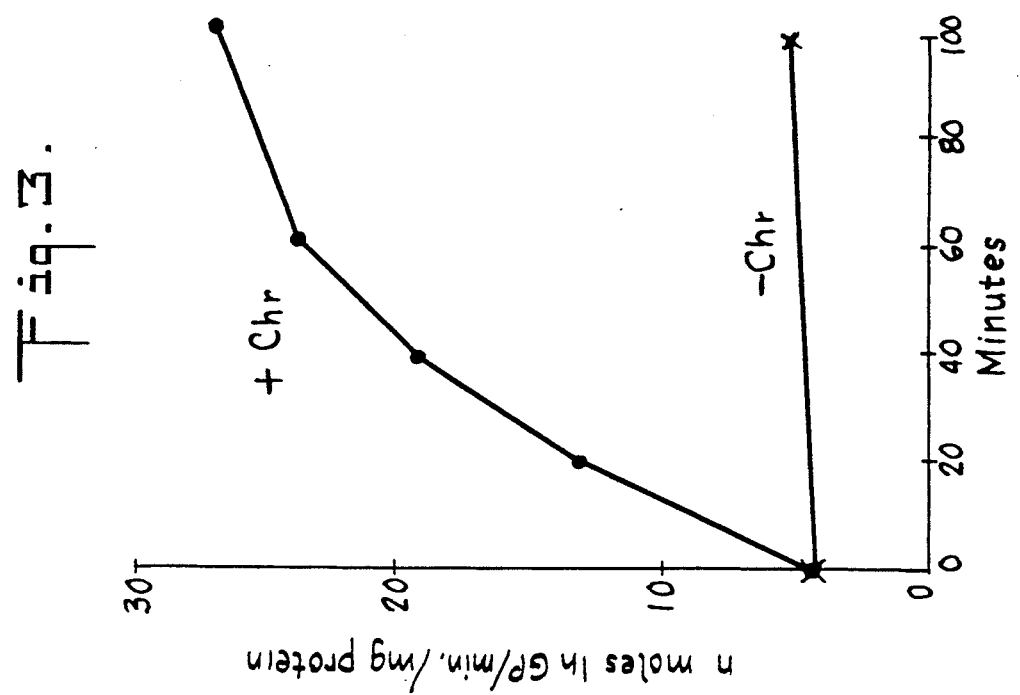
FIG. 3 shows induction by chloramphenicol of InGPS specified by pPL608-5. BD224 (pPL608-5) was grown to the middle of the exponential growth phase in Min CH containing 100 μg per ml of tryptophan. The culture was split and 50 ml samples were withdrawn from each. A subinhibitory concentration of Chr (0.1 μg/ml) was added to one culture, and during subsequent growth, 50 ml samples were periodically withdrawn. Cells in each sample were harvested, processed and assayed for InGPS as described in Hoch, S. O. and Crawford, I. P., J. Bacteriol. 116:685-693 (1973).

The CAT activity specified by pPL608 was 10-fold higher in host cells grown in the presence of Chr than in the same cells grown in drug free broth [Williams, D. M., et al., J. Bacteriol. 146:1162–1165 (1981)]. This increase is believed to result from Chr induction of CAT. It was thought therefore that the expression of foreign genes, such as the *E. coli* trpC fragment, inserted into the CAT gene might also be inducible by Chr. BD224 (pPL608-5) was grown to the middle of the exponential growth phase in Min CH containing 100 µg/ml of tryptophan. The culture was split and a concentration of Chr which is subinhibitory to BD224, 0.1 µg/ml, was added to one. Within 100 min after addition of Chr to BD224 (pPL608-5), a 7-fold increase in the level of the trpC gene product InGPS was detected (as shown in FIG. 3). BD224 (pPL608-5) not exposed to Chr showed no increase in the specific activity of InGPS (FIG. 3). In contrast to the apparent induction of the cloned trpC expression by Chr, the expression of the cloned trpC appeared unaffected by the level of tryptophan added to the growth medium. BD224 (pPL608-5) grown in Min CH or Min CH containing 0.5 µg/ml of tryptophan or 200 µg/ml of tryptophan contained approximately the same level of InGPS.

EXPRESSION OF MOUSE DHFR CLONED IN *B. SUBTILIS*

In order to test whether pPL608 would allow expression of a cloned eucaryotic gene, the mouse gene specifying DHFR previously cloned in *E. coli* on a PstI fragment
was chosen [Chang, A. C. Y., et al., Nature 275:617–624 (1978)].

Figure 4:
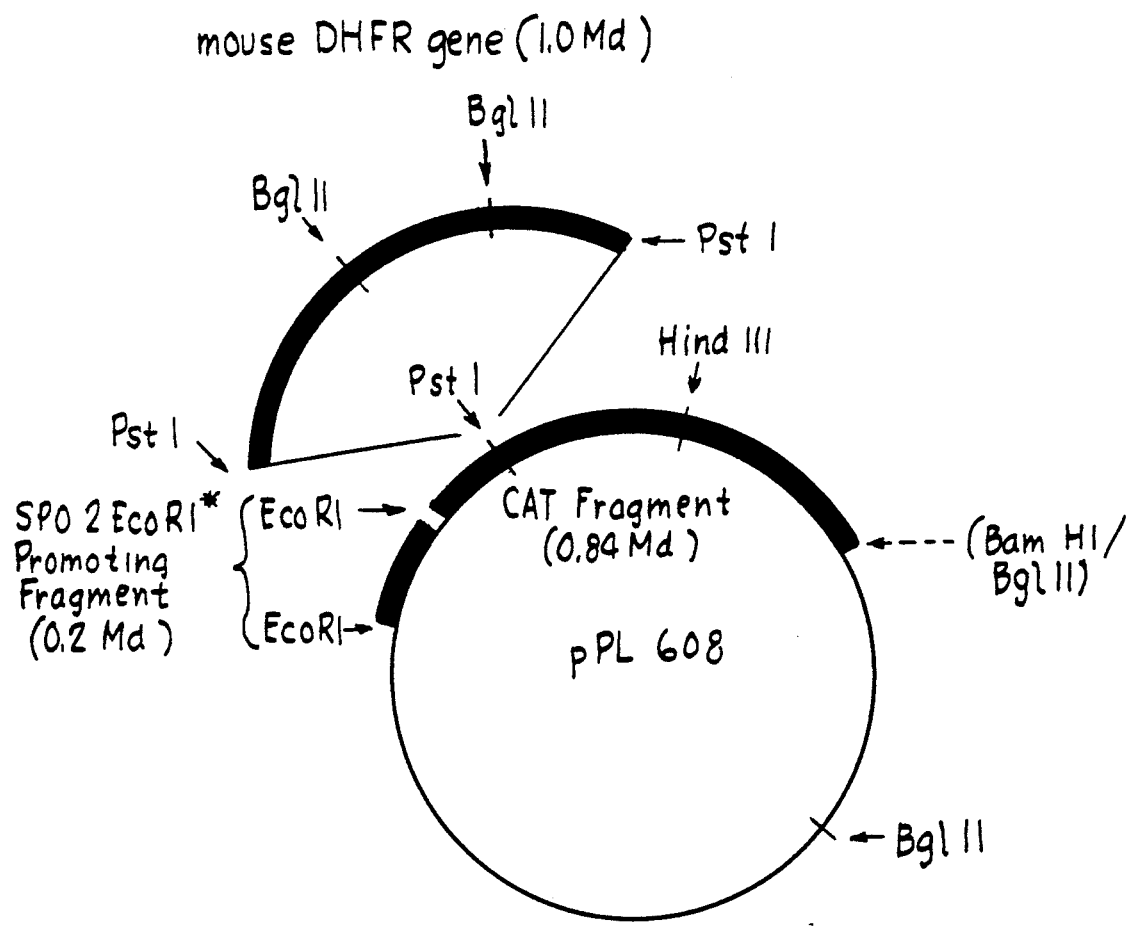
FIG. 4 is a diagram of pPL608-TRI. Orientation of the PstI fragment was deduced from PstI and Bgl II double digests.

Mammalian DHFR is resistant to the drug trimethoprim whereas the bacterial enzyme is sensitive. Selection of cells that were capable of expressing the mouse DHFR gene was therefore based on their resistance to 25 µg/ml of trimethoprim. pPL608-TRl was a derivative of pPL608 containing to 1.0 Md mouse DHFR gene inserted at the PstI site (as shown in FIG. 4) and confirmed by agarose gel electrophoresis of PstI and BglII digested pPL608-5 and pDHFR11 which showed the 1.0 Md PstI mouse DNA fragment present in both pPL608-5 and pDHFR11. Each of more than 200 neomycin-resistant transformants of *B. subtilis* strain BGSCIS53 with pPL608-TRl were resistant to 25 µg/ml of trimethoprim. Removal of either the promoting fragment from pPL608-Trl (by EcoRI) cleavage) on the mouse DHFR fragment (by PstI cleavage) resulted in deleted plasmid forms that no longer specified trimethoprim resistance in strainBGSCIS53. pPL608-TRl confers Chr$^r$ indicating insertion of the fragment of mouse DNA into the PstI site did not inactivate the CAT gene on pPL608.

DHFR activity in extracts of ASB298 (pPL608-TRl) was insensitive to $10^{-6}$ M trimethoprim, but was reduced by 93 percent when $10^{-6}$ M methotrexate was present in the reaction mixture (shown in Table II). The sensitivity to methotrexate, and resistance to trimethoprim, are characteristics typical of mammalian DHFR [Chang, A. C. Y., et al., Nature 275:617–624 (1978)]. The level of DHFR was similar regardless of whether BESCIS53 (pPL608-TRl) cells were grown in no Chr or 0.1 µg Chr. These data suggest that expression of a gene inserted at the PstI site is not Chr inducible.

TABLE II

| DHFR ACTIVITY IN EXTRACTS OF *B. SUBTILIS* HARBORING pPL608-TR1$^c$ | | |
|---|---|---|
| Inhibitors Added | % Activity Remaining | CPM |
| none | 100% | 3614 |
| Trimethoprim ($10^{-6}$M) | 100% | 3626 |
| Trimethoprim ($10^{-6}$M) + | 7% | 247 |

TABLE II-continued

DHFR ACTIVITY IN EXTRACTS OF
B. SUBTILIS HARBORING pPL608-TR1[c]

| Inhibitors Added | % Activity Remaining | CPM |
|---|---|---|
| Methotrexate ($10^{-6}$M) | | | c. BGSCIS53 (pPL608-TR1) cells were grown in penassay broth and harvested during mid exponential growth. Cells were washed and resuspended in 0.1 M KHPO$_4$, pH 5.8, and extracts prepared as described for CAT [Shaw, W. V., Methods Enzymol. 43:737-755 (1975)]. Assays for DHFR [Littlefield, J. W., Proc. Natl. Acad. Sci., USA, 62:88-95 (1969)] were done in duplicate and varied by no more than ±5 percent. DHFR activity assayed without inhibitors equaled 1.5 units where 1.0 unit will convert 1 Nmole of folate to tetrahydrofolate per minute at 37° C.

pPL608 appears to be a valuable vector for achieving foreign gene expression in B. subtilis. The present study demonstrates Chr inducible expression of a foreign procaryotic gene inserted at the Hind III site and expression of the mouse DHFR gene inserted at the PstI site. Moreover, the promoter fragment within pPL608 is readily removed from the plasmid allowing for the insertion of other promoters that may enhance or reduce the expression of cloned foreign genes.

The 1.7 Md Hind III E. coli trp fragment cloned in pPL608 from chromosome digest or from pVH5 was identified by complementation of a genetic defect in the recipient. The cloned fragment complements mutations in the B. subtilis trp genes D, C, and F. It has been previously shown that two Hind III sites occur within the E. coli trp operon flanking the E. coli trpC(F) gene [Crawford, I. P., et al., J. Mol. Biol. 142:489-502 (1980); Nichols, B. P., et al., J. Mol. Biol. 142:503-517 (1980); and Christie, G. E. and Platt, T. J. Mol. Biol. 142:159-530 (1980)]. One site is located in the beginning of trpB and the other is approximately in the middle of trp(G)D. The E. coli trpC(F) gene specifies a protein that has two activities, each of which is specified by a separate gene in B. subtilis, trpC and trpF [Crawford, I. P., Bacteriol. Rev. 39:87-120 (1975)]. The E. coli trp(G)D cistron specifies a protein that also exhibits two activities, each of which is specified by a separate gene in B. subtilis, trpG and trpD [Crawford, I. P., Bacteriol. Rev. 39:87-120 (1975)]. Since the cloned E. coli fragment complements a mutation in the B. subtilis trpD gene, that portion of the E. coli trp(G)D gene corresponding to the B. subtilis trpD gene is being expressed. The trpD activity is associated with the carboxy terminal portion of the trp(G)D product, and the corresponding portion of the gene is present on the cloned fragment. The translation initiation codon necessary for trpD expression may reside in the plasmid vector, and may result in the fusion of the amino terminal portion of a vector specified protein (probably CAT) to the carboxy terminal peptide specified by the cloned trpD gene.

Expression of the CAT gene in pPL608, the trpC gene in pPL608-5 or the DHFR gene in pPL608-TR1 was dependent on the presence of the promoter fragment. Therefore, the promoter fragment likely provides sequences necessary for transcription initiation and that transcription occurs from the promoting fragment through the CAT structural gene. Insertion of genes between the PstI and Hind III sites on pPL608 presumably places them under control of a strong promoter that is efficiently recognized by B. subtilis RNA polymerase.

Production of polypeptide upon expression of the cloned mouse DHFR gene has been confirmed. Initial molecular weight characterization established that the enzyme DHFR was in fact produced.

In summary, the mouse dihydrofolate reductase gene and a segment of the Escherichia coli trp operon genetically express in Bacillus subtilis when cloned in the novel plasmid pPL608. The cloned mouse gene confers trimethoprim resistance on B. subtilis and the cloned trp fragment complements mutations in the B. subtilis trp D C and F genes. Expression of both cloned fragments is dependent on a promoter present in the vector plasmid. The E. coli trp fragment is cloned in a Hind III site within a chloramphenicol acetyltransferase gene present on pPL608, and as a result, expression of the E. coli trpC gene product is inducible by chloramphenicol. The mouse gene is inserted at a PstI site preceding the chloramphenicol acetyltransferase gene and its expression is not chloramphenicol inducible. The replication functions and neomycin-resistance of pPL608 are derived from pUB110. Accordingly, pPL608 is stably maintained at high copy number in B. subtilis.

MATERIALS AND METHODS

Bacteria, plasmids and media

Strains of B. subtilis and E. coli used are listed in Table III. Plasmids pUB110, pCM194, pVH5 and pBR322 have been described [Bolivar, F., et al., Gene 2:95-113 (1977); Gryczan, T. J., et al., J. Bacteriol. 134:318-323 (1978); and Hershfield, V., et al., Proc. Natl. Acad. Sci., U.S.A. 71:3455-3459 (1974)]. pDHFR11 is a pBR322 derivative containing a 1.0 Md PstI fragment specifying mouse dihydrofolate reductase [Chang, A. C. Y., et al., Nature 275:617-624 (1978)]. Tryptose blood agar base and penassay broth were from Difco. Min-CH medium has been described [Spizizen, J. Proc. Natl. Acad. Sci., U.S.A. 44:1072-1078 (1958)]. Minimal agar for E. coli was M9. All incubations were at 37° C.

Enzyme assays

CAT was assayed as described by Shaw [Shaw, W. V., Methods Enzymol. 43:737-755 (1975)]. InGPS was assayed according to the methods of Hoch and Crawford [Hoch, S. O. and Crawford, I. P., J. Bacteriol. 116:685-693 (1973)], and DHFR was measured by the procedure of Littlefield. [Littlefield, J. W., Proc. Natl. Acad. Sci., U.S.A. 62:342-357 (1969)]. The Bradford method was used for protein determinations. [Bradford, M., Anal. Biochem. 72:248-254 (1976)].

Expression plasmid pPL608

The construction of pPL608 is described hereinabove and in Williams, D. M., et al., J. Bacteriol. 146:1162-1165 (1981)]. The plasmid has a mass of about 3.3 Md and consists of a major portion of pUB110 joined to a 0.8 Md segment of B. pumilus DNA containing a CAT gene plus a 0.2 Md EcoRI* promoter fragment cloned from phage SP02 DNA. The cloned promoter permits expression of the CAT gene, thereby allowing pPL608 to confer Chr[r] on B. subtilis. Unique restriction sites for Hind III and PstI exist downstream from the promoter (see FIG. 2).

The specific activity of CAT in BR151 (pP:608) was 10-to 20-fold higher in cells grown in Chr (5 μg/ml) than in cells grown in drug free broth. The molecular size and copy number (approximately 50) were the same regardless of whether host cells were grown in the presence or absence of Chr. Thus, the increased CAT activity was not due to increased gene doseage. Exposure of BD224 (pPL608) to a subinhibitory concentration of CHr (0.1 μg/ml) caused a 10-fold increase in the specific activity of CAT within 100 minutes. It therefore appears that CAT is inducible by Chr.

TABLE III

| BACTERIAL STRAINS | | |
|---|---|---|
| Organism | Strain | Relevant properties |
| B. subtilis 168 | Br151 | trpC2 metB10 lys-3 |
| | BD224 | trpC2 thr-5 recE4 |
| | T4 | trpA |
| | T20 | trpB |
| | T12 | trpF |
| | T5 | trpC |
| | T22 | trpD |
| | T24 | trpE |
| | BGSCIS53 | spoOAΔ677 |
| E. coli | HB101 | Trp+ |
| | IC888 | trpC |

CLONING ESCHERICHIA COLI trpC IN B. SUBTILIS

Hind III digests of HB101 chromosome DNA (2 μg) or plasmid pVH5 (1 μg) were combined with 0.5 μg of Hind III cleaved pPL608, annealed, ligated [Lovett, P. S. and Keggins, K. M., Methods Enzymol. 68:342–357 (1979)] and transformed into competent BD224 [Bott, K. F. and Wilson, G. A., J. Bacteriol. 94:562–570 (1967)] at 1 μg/ml of DNA. Cells were plated on Min CH containing 10 μg/ml of neomycin sulfate. Fourteen Trp+ transformants were recovered by cloning from HB101 DNA, and 93 were obtained by cloning from pVH5. pPL608-3 and pPL608-5 are Trp+ derivatives of pPL608 containing Trp inserts from HB101 and pVH5, respectively. The ability of the cloned trp fragment to complement mutations in each of the six B. subtilis trp genes was performed as previously described. [Keggins, K. M., et al., Proc. Natl. Acad. Sci., U.S.A. 75:1423–1427 (1978)]. Southern transfers, nick translation, hybridizations and agarose gel electrophoresis were as previously described [Marrero, R. and Lovett, P. S., J. Bacteriol. 143:879–886 (1980); and Southern, E. M., J. Mol. Biol. 98:503–517 (1975)].

CLONING MOUSE DIHYDROFOLATE REDUCTASE (DHFR) IN B. SUBTILIS pDHFR11 (1 μg/ml) and pPL608 (1 μg/ml) were digested with PstI annealed ligated and transformed into B. subtilis strain BGSCIS53. Neomycin-resistant transformants were selected and each was picked to appropriately supplemented Min CH containing 25 μg/ml of trimethoprim. Approximately 2 percent of the transformants were tri-methoprim resistant. The plasmid from one such clone, pPL608-TR1, was characterized.

What is claimed is:

1. A plasmid for introducing foreign DNA into B. subtilis, said plasmid comprising a double-stranded DNA molecule which includes a promoter active in B. subtilis selected from the group consisting of bacteriophage SPO2, bacteriophage Φ105, plasmid pPL10 and B. licheniformis promoters, wherein said promoter is for controlling expressionn of said foreign DNA when the plasmid is present in B. subtilis, and which plasmid includes a DNA fragment encoding a chloramphenicol acetyltransferase gene from B. pumilus NCIB 8600 as a selectable marker.

2. The plasmid of claim 1 wherein said fragment encoding the chloroamphenicol acetyltransferease gene is from a plasmid selected from the group consisting of pPL603, pPL601, and pPL531.

3. A plasmid for effecting control of expression of foreign DNA in B. subtilis wherein said foreign DNA has a nucleic acid sequence that doces for a polypeptide product, said plasmid comprising a double-stranded DNA molecule wherein said foreign DNA is operably linked to a promoter active in B. subtilis selected from the group consisting of bacteriophage SPO2, bacteriophage 101105, plasmid pPL10 and B. licheniformis promoters, wherein said promoter effects expression of said foreign DNA when the plasmid is present in B. subtilis, and which plasmid includes a DNA fragment encoding a chloramphenicol acetyltransferase gene from B. pumilus NCIB 8600 as a selectable marker.

4. A plasmid in accordance with claim 3 wherein the polypeptide is insulin, growth hormone, the polypeptide portion of interferon, somatostatin, or an enzyme.

5. A plasmid in accordance with claim 3 wherein the foreign DNA is a mammalian gene.

6. The plasmid cell of claim 3 wherein said fragment encoding the cloramphenicol acetyltransferase gene is from a plasmid selected from the group consisting of pPL603, pPL601, pPL608 and pPL531.

7. A method of producing a polypeptide product which comprises transforming a B. subtilis cell with the plasmid of any one of claims 3, 4 or 5, growing said cellunder suitable conditions to effect expression of said foreign DNA and thereby production of said product, and recovering the product so produced.

8. A B. subtilis cell which contains a plasmid in accordance with any of claims 1, 3, 4 or 5.

9. A plasmid for identifying B. subtilis-active promoters to control expression of foreign DNA which comprises a DNA fragment of B. pumilus strain NCIB 8600 coding for the chloramphenicol acetyltransferase gene with restriction endonuclease sites positioned such that a second DNA fragment coding for a promoter active in B. subtilis can be joined to the second fragment which is thereby operably linked to said chloramphenicol acetyltransferase gene to control expression of said chloramphenicol acetyltransferase gene.

10. Plasmid pPL603 having the restriction map shown in FIG. 1.

11. Plasmid pPL601 having the restriction map shown in FIG. 1

12. Plasmid pPL531 having the restriction map shown in FIG. 1.

13. Plasmid pPL604 formed by inserting a 1.3 megadalton EcoRI* fragment of pUB110 into pPL603.

14. Plasmid pPL605 formed by inserting a 0.54 megadalton EcoRI* fragment of pPL10 into pPL603.

15. Plasmid pPL608 formed by inserting a 0.21 megadalton EcoRI* fragment of SPO2 into pPL603.

16. Plasmid pPL613 formed by inserting a 0.15 megadalton EcoRI fragment of B. licheniformis DNA into pPL603.

17. Plasmid pPL614 formed by inserting a 1.0 megadalton EcoRI fragment of B. licheniformis DNA into pPL603.

* * * * *

UNITED STATES PATENT AND TRADEMARK OFFICE
CERTIFICATE OF CORRECTION

PATENT NO. : 5,162,206

DATED : November 10, 1992

INVENTOR(S) : Paul S. Lovett

Page 1 of 2

It is certified that error appears in the above-identified patent and that said Letters Patent is hereby corrected as shown below:

On the title page:

In the Abstract, line 6: "does" should read --codes--

Column 5, line 47: "EcoRI*" should begin a new paragraph.

Column 6, line 4: "recE4" should read --recE4--

Column 6, line 66: after "described" delete --.--

Column 8, line 40: "resustant" should read --resistant--

Column 8, line 41: after "BGSCIS53" insert --generated--

Column 8, line 59: "ug Chr" should read --ug/ml of Chr--

Column 8, line 68: delete "7% 247"

Column 9, line 6: insert --7% 247--

Column 9, line 16: "Nmole" should read --nmole--

UNITED STATES PATENT AND TRADEMARK OFFICE
CERTIFICATE OF CORRECTION

PATENT NO. : 5,162,206
DATED : November 10, 1992
INVENTOR(S) : Paul S. Lovett

It is certified that error appears in the above-identified patent and that said Letters Patent is hereby corrected as shown below:

Column 9, line 38:  "159"  should read --519--
Column 12, line 4, Claim 2:  "acetyltransferease" should read --acetyltransferase--
Column 12, line 6, Claim 2:  after "pPL601" insert --pPl608--
Column 12, line 9, Claim 3:  "doces" should read --codes--
Column 12, line 14, Claim 3:  "101105" should read --ö 105--
Column 12, line 25, Claim 6:  delete "cell"
Column 12, line 32, Claim 7:  "cellunder" should read --cell under--

Signed and Sealed this

Twenty-eighth Day of December, 1993

Attest:

BRUCE LEHMAN

Attesting Officer

Commissioner of Patents and Trademarks